(12) United States Patent
Kendall et al.

(10) Patent No.: US 8,968,654 B2
(45) Date of Patent: Mar. 3, 2015

(54) FLUID DELIVERY SYSTEM AND LIFT FOR USE IN CONJUNCTION THEREWITH

(71) Applicants: Thomas Matthew Kendall, Johnston, RI (US); Matthew Charles Tierney, West Roxbury, MA (US); Joseph Scott Cantara, North Attleboro, MA (US)

(72) Inventors: Thomas Matthew Kendall, Johnston, RI (US); Matthew Charles Tierney, West Roxbury, MA (US); Joseph Scott Cantara, North Attleboro, MA (US)

(73) Assignee: Automation Solutions, Inc., Beverly, MA (US)

( * ) Notice: Subject to any disclaimer, the term of this patent is extended or adjusted under 35 U.S.C. 154(b) by 211 days.

(21) Appl. No.: 13/738,196

(22) Filed: Jan. 10, 2013

(65) Prior Publication Data
US 2013/0343851 A1    Dec. 26, 2013

Related U.S. Application Data

(60) Provisional application No. 61/662,741, filed on Jun. 21, 2012.

(51) Int. Cl.
| | |
|---|---|
| *B66F 7/14* | (2006.01) |
| *B66F 7/12* | (2006.01) |
| *B66F 7/02* | (2006.01) |
| *B01L 3/02* | (2006.01) |
| *B01L 9/00* | (2006.01) |
| *G01N 35/10* | (2006.01) |

(52) U.S. Cl.
CPC ... *B66F 7/12* (2013.01); *B66F 7/14* (2013.01); *B01L 3/0293* (2013.01); *B01L 9/00* (2013.01); *G01N 35/1002* (2013.01); *B01L 2400/0457* (2013.01)

USPC ......... 422/63; 414/590; 414/680; 414/744.3; 248/127; 248/405

(58) Field of Classification Search
None
See application file for complete search history.

(56) References Cited

U.S. PATENT DOCUMENTS

| | | | |
|---|---|---|---|
| 2,950,829 A | 8/1960 | McBean et al. | |
| 4,180,074 A * | 12/1979 | Murry et al. | 604/31 |
| 4,719,087 A * | 1/1988 | Hanaway | 422/551 |
| 5,750,074 A * | 5/1998 | Katzman et al. | 204/601 |
| 7,708,946 B1 | 5/2010 | Sherman et al. | |
| 7,871,470 B2 * | 1/2011 | Schieve et al. | 118/728 |
| 2004/0116846 A1 | 6/2004 | Olivera et al. | |
| 2008/0265120 A1 | 10/2008 | Altshuler et al. | |

FOREIGN PATENT DOCUMENTS

WO        0045164 A1    8/2000

* cited by examiner

*Primary Examiner* — Jill Warden
*Assistant Examiner* — Benjamin Whatley
(74) *Attorney, Agent, or Firm* — Kriegsman & Kriegsman (57) ABSTRACT

A fluid delivery system includes a laboratory instrument that operates using fluid retained in one or more containers. The containers are supported on a motor-driven lift that is configured to transport the containers between a lowered position suitable for handling and an elevated position suitable for the delivery of fluid to the instrument by gravity. The lift includes a bench-mountable base, a tubular column extending upward from the base, an elongated lead screw extending longitudinally through the column, a drive mechanism for rotatably driving the lead screw, a carriage slidably mounted over the tubular column and mechanically coupled to the lead screw, a platform removably coupled to the carriage for supporting the containers, and a control system for regulating operation of the drive mechanism. During operation, a slot provided in the column restricts travel of the platform along a predefined path that is linear in part and helical in part.

18 Claims, 12 Drawing Sheets

FLUID DELIVERY SYSTEM AND LIFT FOR USE IN CONJUNCTION THEREWITH

FIELD OF THE INVENTION

The present invention relates generally to laboratory analytic equipment and more particularly to accessories for laboratory analytic equipment.

BACKGROUND OF THE INVENTION

In chemical laboratories, analytic instruments are commonly utilized to determine, inter alia, the mass, elemental composition and/or chemical structure of a sample. Examples of laboratory analytical instruments that are commonly utilized to determine properties associated with a sample include, but are not limited to, liquid chromatography units and mass spectrometers.

Certain types of laboratory instruments utilize one or more fluids, such as common solvents, to modify chemical aspects of the sample as part of its analytical process. The fluids are traditionally retained within one or more bottles, or other similar containers, that are in turn fed into components of the analytic instrument by conduits, such as plastic tubing. In certain applications, the bottles of solution are disposed above the analytic instrument and rely, at least in part, upon gravity to promote delivery of the fluid into the instrument.

Gravity feeding of fluids into laboratory analytic instruments is traditionally achieved using a shallow, nearly flat, tray, or other similar platform, that is placed directly on the top surface of the particular analytic device. The tray is typically dimensioned to receive a certain number, style and shape of bottles thereon. Due to its shallow construction, such a tray is also commonly provided with one or more drainage openings that are provided to prevent the overflow of fluids that accumulate thereon as a result of spillage from the bottles. A drainage system is then preferably disposed in communication with each opening to safely collect the spilled fluids.

Although well-known in the art, the use of trays to support containers of fluid for laboratory analytic equipment has been found to suffer from a number of notable drawbacks.

As a first drawback, trays used to support containers of fluid for laboratory analytic equipment are typically maintained at a considerable height, especially when the analytic instrument on which it is mounted is in turn disposed on top of a laboratory bench. In fact, it has been found that many trays used to hold fluid for laboratory analytic equipment are often disposed several feet above the flooring surface. As a consequence, it has been found that laboratory technicians are often unable to safely access containers that need to be replaced and/or refilled. Rather, technicians in certain circumstances resort to climbing within the laboratory (e.g., using a stool, chair or the like), which inherently creates an unsafe environment for both the technician as well as the equipment.

As a second drawback, it has been found that the use of trays to support containers of fluid for laboratory analytic equipment can render the routine inspection of the containers to assess fluid levels rather difficult. Specifically, as noted briefly above, trays are traditionally disposed directly on top of its associated instrument which is, in turn, often positioned on a laboratory bench or other similar structure. As a result of the height of the tray and its position directly on top of its associated instrument, laboratory technicians are often unable to routinely inspect fluid levels, which is highly undesirable since many instruments require frequent bottle servicing.

As a third drawback, the use of a relatively shallow tray requires the inclusion of drainage openings to prevent the overflow of accumulated fluids. However, if the system suffers from any drainage malfunctions or imperfections, there is an increased risk that spilled solvents, often toxic in nature, can fall into contact with laboratory personnel and/or equipment, which is highly undesirable.

As a fourth drawback, each tray is traditionally manufactured for a designated instrument. Accordingly, each tray is typically provided with a footprint that roughly corresponds to the dimensions of the exposed top surface of its associated instrument. Furthermore, the top surface of each tray is typically shaped to retain a certain number, style and shape of bottles that is optimized for the instrument with which it is to be used. Due to the inherent inflexibility in its design, each tray is typically rendered unusable with other types of instruments. Rather, it is generally required that a specific bottle support tray be purchased for each type of gravity fed, analytic instrument used in a laboratory, thereby significantly increasing overall costs, which is highly undesirable.

SUMMARY OF THE INVENTION

It is an object of the present invention to provide a new and improved system for delivering fluid retained in one or more bottles to a laboratory analytic instrument, at least in part, by means of gravity.

It is another object of the present invention to provide a system as described above that includes a device for supporting the bottles of fluid.

It is yet another object of the present invention to provide a system as described above wherein the device renders the bottles of fluid easily accessible for handling.

It is still another object of the present invention to provide a system as described above wherein the device allows for the level of fluid in each of the bottles of fluid to be readily visually ascertained.

It is yet still another object of the present invention to provide a system as described above wherein the device is designed to safely collect fluid inadvertently spilled from the one or more bottles.

It is even still another object of the present invention to provide a system as described above wherein the device has a limited workspace footprint, includes a minimal number of parts, is durable in its construction, is easy to use and is inexpensive to manufacture.

Accordingly, as a principal feature of the present invention, there is provided a fluid delivery system, comprising (a) a container filled with a fluid; (b) a laboratory instrument adapted to receive the fluid; (c) a lift for supporting the container, wherein the lift is adapted to transport the container between a lowered position suitable for handling the container and an elevated position suitable for the delivery of the fluid to the laboratory instrument by gravity.

Various other features and advantages will appear from the description to follow. In the description, reference is made to the accompanying drawings which form a part thereof, and in which is shown by way of illustration, an embodiment for practicing the invention. The embodiment will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF THE INVENTION

Fluid Delivery System 11

Figure 1:
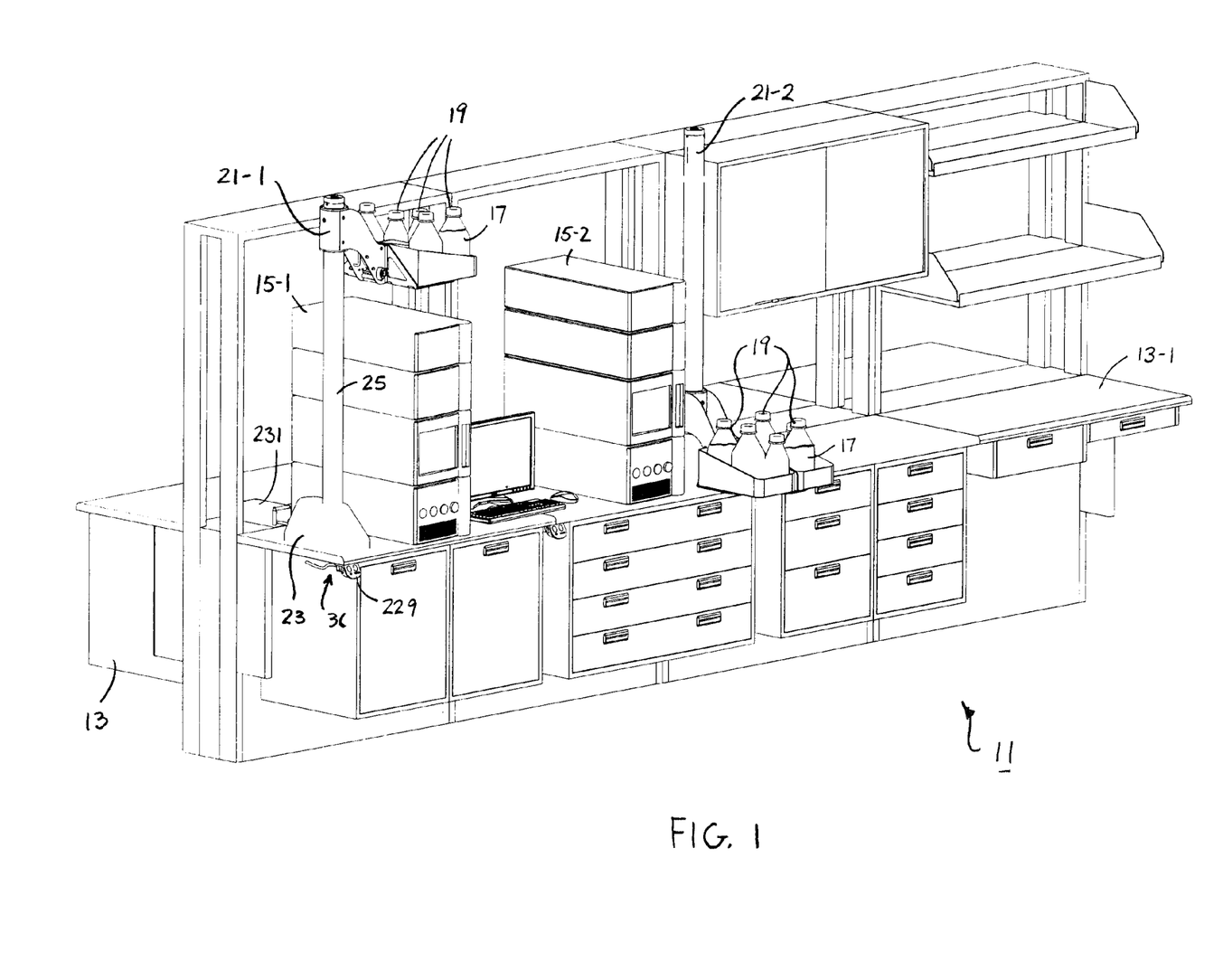
FIG. 1 is a front perspective view of a fluid delivery system constructed according to the teachings of the present invention.

Referring now to FIG. 1, there is shown a fluid delivery system constructed according to the teachings of the present invention, the fluid delivery system being identified generally by reference numeral 11. As will be described in detail below, system 11 is designed primarily to improve safety in laboratory environments that rely upon gravity to feed fluids into test equipment.

As shown herein, fluid delivery system 11 comprises a support structure 13, first and second laboratory analytic devices, or instruments, 15-1 and 15-2 disposed on support structure 13, each device 15 relying upon the delivery of a fluid 17 via gravity during normal operation, a plurality of containers 19, each container 19 being dimensioned to retain a supply of fluid 17, and first and second lifts 21-1 and 21-2 mounted on support structure 13, each lift 21 being adapted to support one or more containers 19 for a corresponding device 15. As will be described in detail below, each lift 21 is designed to move containers 19 supported thereon between a first, or lowered, position in which containers 19 are rendered highly accessible for inspection and/or replacement and a second, or elevated, position in which containers 19 are disposed directly above its corresponding device 15 and thereby enable fluid 17 to be gravity fed into its associated device 15 via tubular conduits (not shown). Accordingly, it is to be understood that the inclusion of each lift 21 within system 11 serves as a principal novel feature of the present invention.

In the present embodiment, two complementary pairs of devices 15 and lifts 21 are shown mounted on support structure 13. However, it is to be understood that system 11 is not limited to a particular number of complementary pairs of devices 15 and lifts 21. Rather, a fewer or greater number of complementary pairs of devices 15 and lifts 21 could be mounted on support structure 13 without departing from the spirit of the present invention.

Support structure 13 is represented herein as a conventional, laboratory bench that includes an enlarged bench top, or workspace, 13-1 on which devices 15 and lifts 21 are disposed. As defined herein, support structure 13 represents any enlarged, preferably flattened surface that is suitable for supporting devices 15, lifts 21 and other necessary items.

Although not shown herein, it is to be understood that fluid delivery system 11 could be alternatively designed without support structure 13. For instance, in certain circumstances, it is envisioned that devices 15 and lifts 21 could be floor mounted, thereby eliminating the need for support structure 13.

As defined herein, device 15 represents any instrument that relies upon the delivery of fluid 17 via gravity, such liquid chromatography units, mass spectrometers and other similar types of solution-based, laboratory analytical instruments. Because lift 21 has a minimal bench top footprint and is designed to promote the safe handling of chemical solutions, system 11 has a particular usefulness in laboratory environments. However, it is to be understood that alternative applications for lift 21 could be envisioned without departing from the spirit of the present invention.

Construction of Lift 21-1

As noted briefly above, each lift 21 is designed to mechanically transport one or more containers 19 of fluid 17 between a lowered position, which is suitable for operator inspection and handling, and an elevated position, which is suitable for the gravity feeding of fluid 17 into its corresponding device 15. As such, the construction of lift 21 and its operation within system 11 serve as the primary novel features of the present invention.

Referring now to FIGS. 1 and 2(a)-(c), lift 21-1 comprises a base 23 adapted to be mounted on bench top 13-1 of support structure 13, a hollow tubular column 25 mounted on base 23, an elongated lead screw 27 extending longitudinally within column 25 in a coaxial relationship relative thereto, a cap assembly 29 mounted onto column 25 for holding lead screw 27 in place within column 25, a motorized drive mechanism 31 coupled to base 23 for rotatably driving lead screw 27 within column 25, a carriage 33 slidably mounted over tubular column 25 and mechanically coupled to lead screw 27, a platform 35 removably coupled to carriage 33 that is adapted to support one or more containers 19, and a control system 36 for regulating operation of motorized drive mechanism 31. As will be described below, the motor-driven rotation of lead screw 27 displaces carriage 33 and platform 35 along a predefined, multi-planar path between a lowered position and an elevated position.

Figure 3A:
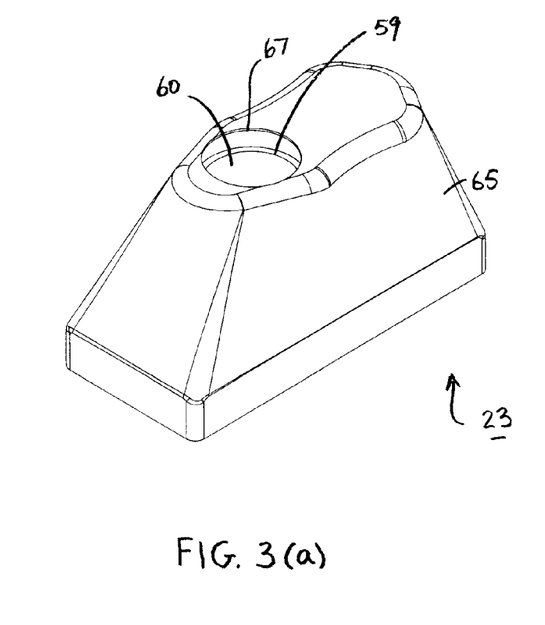
FIGS. 3(a)-(b) are assembled, top perspective and exploded, top perspective views, respectively, of the base shown in FIG. 2(a)
Figure 3B:
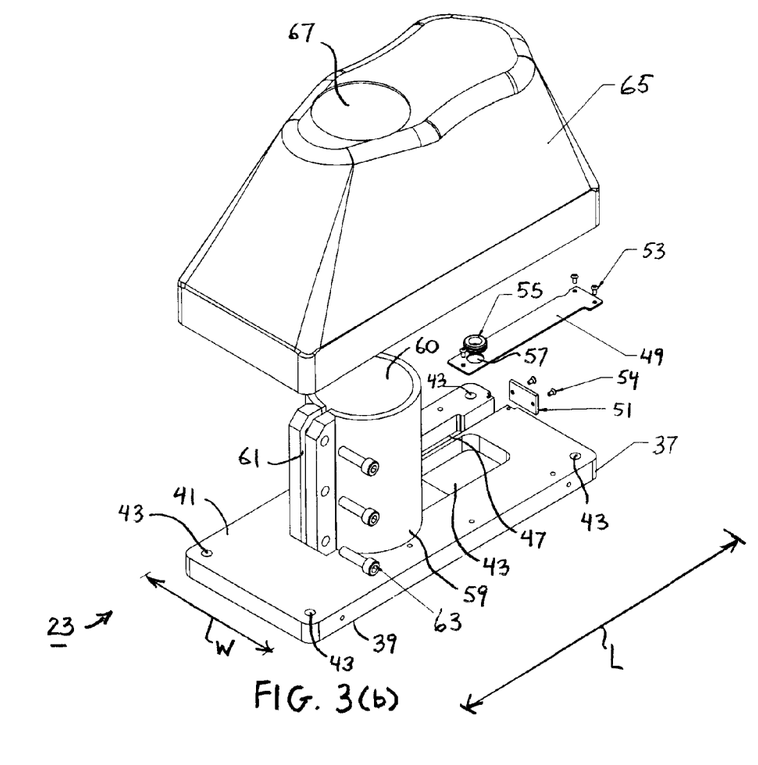

As seen most clearly in FIGS. 3(a) and 3(b), base 23 comprises a support block 37 constructed of a rigid and durable material, such as metal. Support block 37 is a generally rectangular member that includes a flattened bottom surface 39, a flattened top surface 41 and a plurality of transverse bores 43 that are generally circular in transverse cross-section. In this capacity, flattened bottom surface 39 is designed to lie flush on workspace 13-1 and be permanently secured thereto by driving screws (not shown) through bores 43 and into support structure 13.

In the present embodiment, support block 37 preferably has a length L of approximately 350 mm and a width W of approximately 155 mm, the aforementioned dimensions of support block 37 defining the overall footprint for lift 21-1 on workspace 13-1. As can be appreciated, the relatively small footprint required for lift 21-1 maximizes the amount of free, or usable, space on workspace 13-1 and, as such, serves as a feature of the present invention.

Top surface 41 of support block 37 includes a rectangular recess 45 that is dimensioned to receive select components of drive mechanism 31. Support block 37 is also shaped to define a rearward channel 47 that is dimensioned to receive a portion of electrical wiring for lift 21-1, with a thin top cover plate 49 and a thin back cover plate 51 being removably secured to support block 37 by screws 53 and 54, respectively, to selectively enclose channel 47. A rubber grommet 55 is press fit into a corresponding opening 57 in top cover plate 49 and serves as a passageway for wiring into channel 47.

A rigid, cylindrical, clamp-ring type post 59 is welded or otherwise fixedly secured onto top surface 41 of support block 37 and extends orthogonally out therefrom. Post 59 is circular in transverse cross-section and includes a central bore 60 and a dual-flanged, longitudinal slot 61 in communication with bore 60, dual-flanged slot 61 allowing for slight adjustability of the diameter of bore 60 through the tightening or loosening of screws 63 extending transversely therethrough.

A hollowed base cover, or shroud, 65 is mounted over base 23 and serves to enclose components of drive mechanism 31 for protective and aesthetic purposes. Cover 65 includes a circular opening 67 that is similar in dimension and coaxially aligns with central bore 60 in post 59, as seen most clearly in FIG. 3(a).

Referring back to FIGS. 2(a)-(c), tubular column 25 is an elongated, hollow cylindrical member that is preferably constructed of a rigid and durable material, such as metal or plastic. Column 25 is uniform in cross-section along the entirety of its length and includes a first end 69, a second end 71 and an intermediate portion 73 that together define an enlarged interior cavity 74 and a longitudinal axis $L_A$.

Figure 2A:
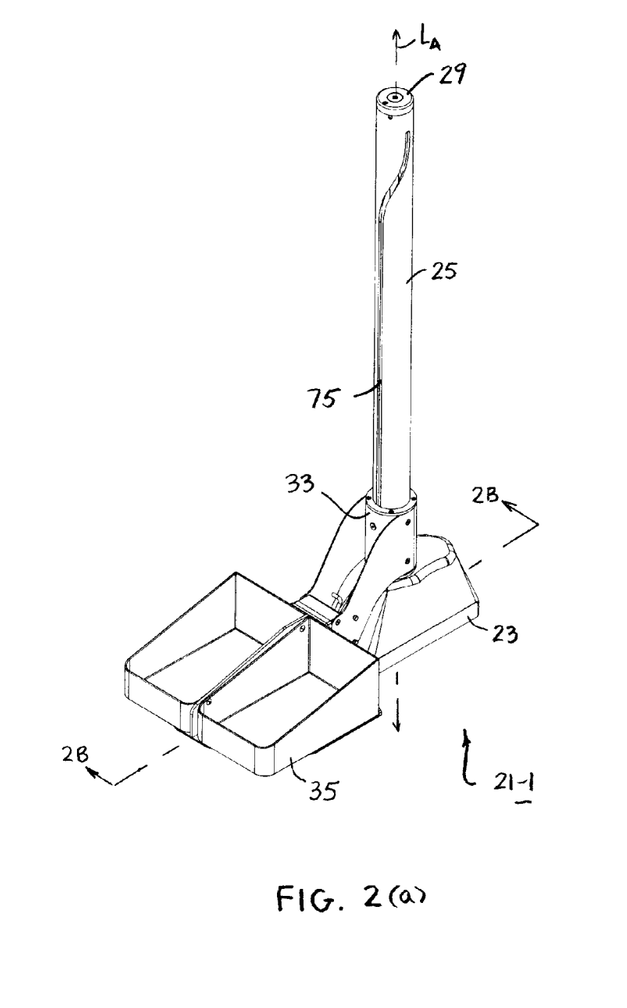
FIG. 2(a) is a front, perspective view of one of the lifts shown in FIG. 1.
Figure 2B:
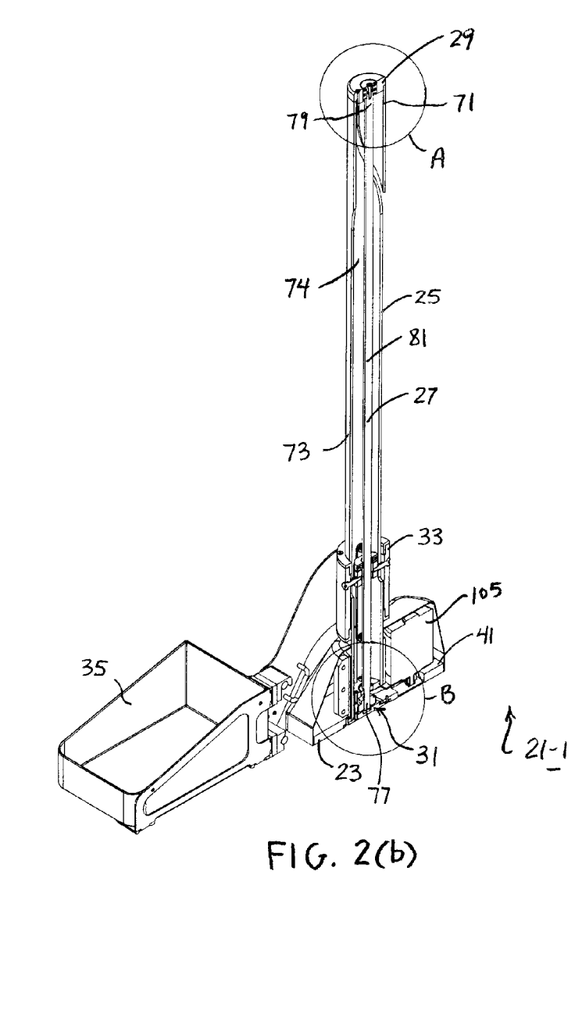
FIG. 2(b) is a front, perspective, section view of the lift shown in FIG. 2(a), taken along lines 2B-2B.
Figure 2C:
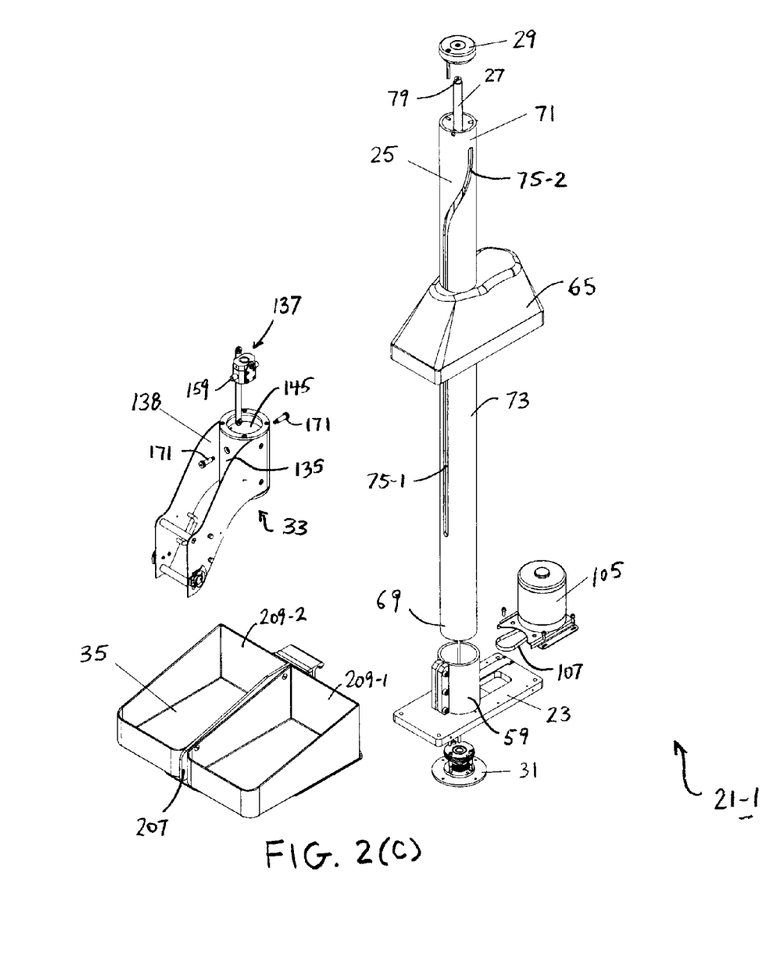
FIG. 2(c) is a partially exploded, front perspective view of the lift shown in FIG. 2(a)

First end 69 of column 25 is dimensioned for fitted insertion through opening 67 in cover 65 and into post 59. By tightening screws 63, first end 69 can be securely retained within post 59 such that column 25 extends vertically upward from top surface 41 of support block 37 in an orthogonal relationship relative thereto.

A pair of elongated, continuous slots 75 is formed into intermediate portion 73 and extends into communication with interior cavity 74. Slots 75 are mirror images of one another when viewed about the longitudinal axis of column 25.

As seen most clearly in FIG. 2(c), each slot 75 includes a first, or straightened, portion 75-1 that is spaced slightly away from first end 69 and extends vertically upward in a linear path along the majority of the length of intermediate portion 73 (i.e., along a path parallel to longitudinal axis $L_A$). A second, or helical, portion 75-2 is formed into intermediate portion 73 that continues from the upper end of straightened portion 75-1 and spirals upward and counterclockwise (approximately 90 degrees) about longitudinal axis $L_A$ to a termination point spaced slightly away from second end 71. As will be described further in detail below, the inclusion and shape of slots 75 enables platform 35 to travel along a defined, multi-planar path that ideal for use in a laboratory setting.

It should be noted that the particular design of each slot 75 causes platform 35 to swivel, or rotate, approximately 90 degrees in the counterclockwise direction (i.e., to the right) about longitudinal axis $L_A$ when traveling to its elevated position, as represented by lift 21-1 in FIG. 1. Accordingly, by reflecting the design of each slot 75 in column 25 about the front-to-back vertical plane, it is to be understood that platform 35 could be reconfigured to swivel approximately 90 degrees in the clockwise direction (i.e., to the left) about longitudinal axis $L_A$ when traveling to its elevated position. Additional alternative configurations of slots 75 could be utilized to further modify the travel path of platform 35 without departing from the spirit of the present invention.

As seen most clearly in FIG. 2(b), lead screw 27 is an elongated screw approximately 0.75 inches in diameter that includes a first end 77, a second end 79 and an externally threaded intermediary section 81, the external threading on intermediary section 81 not being shown in FIGS. 2(b) and 2(c) for ease of illustration purposes only. As noted above, lead screw 27 extends longitudinally through the entire length of interior cavity 74 in a coaxial relationship relative to column 25. Screw 27 is adapted to be rotatably driven about its longitudinal axis which, in turn, drives platform 25 (and any containers 19 mounted thereon) between its lowered and elevated positions, as will be described further below.

Figure 4:
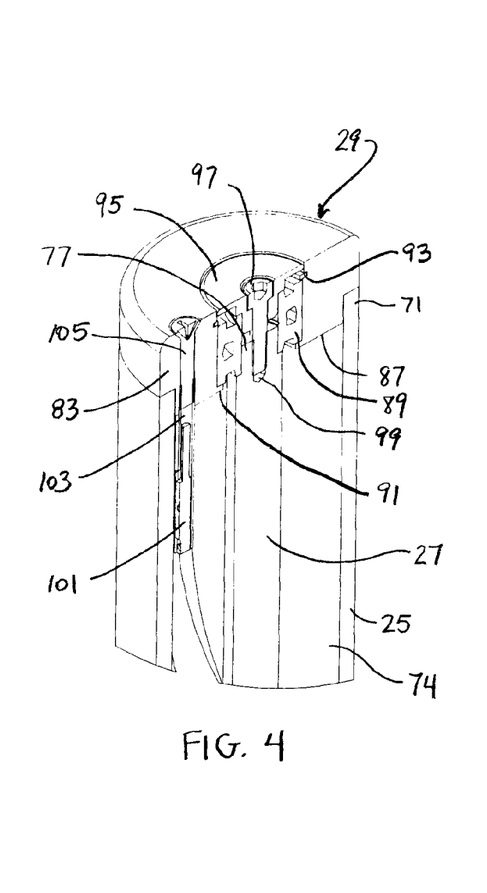
FIG. 4 is an enlarged, fragmentary, section view of the lift shown in FIG. 2(b), taken within the circled region identified by reference letter A.
Figure 5A:
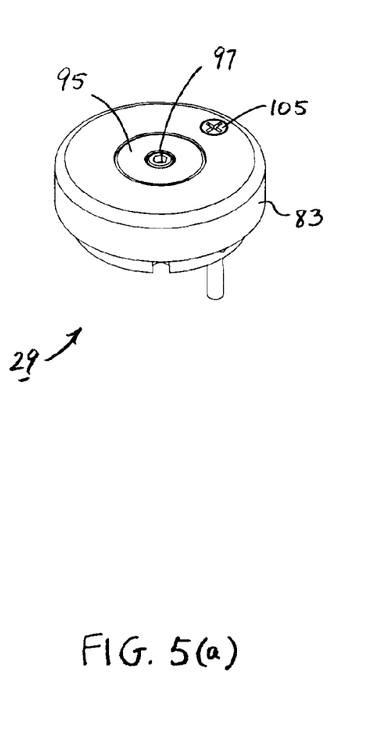
FIGS. 5(a)-(b) are assembled, top perspective and exploded, top perspective views of the cap assembly shown in FIG. 2(b)
Figure 5B:
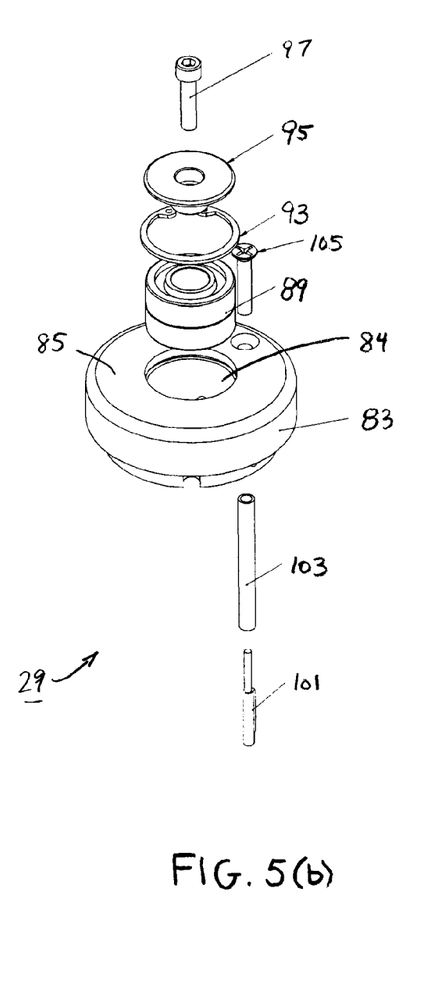

Referring now to FIGS. 4, 5(a) and 5(b), cap assembly 29 is mounted on second end 71 of column 25 and suspends lead screw 27 axially within interior cavity 74. Cap assembly 29 comprises an annular top cap 83 that defines a central opening 84, top cap 83 including a flattened top surface 85 and a flattened bottom surface 87. As seen most clearly in FIG. 4, bottom surface 87 is countersunk to enable top cap 83 to be press fit onto open second end 71 of column 25. Mounted as such, top cap 83 partially encloses second end 71.

An upper bearing 89 is disposed within central opening 84 and allows for rotation of lead screw 27 relative to top cap 83. Upper bearing 89 is generally annular in shape and is press fit into central opening 84 in top cap 83, upper bearing 89 being retained therein by an inwardly extending flange 91 machined into bottom surface 87 of top cap 83 as well as an outwardly-biased, spring retainer ring 93 that projects into a corresponding groove in top cap 83.

A retainer plug 95 substantially encloses annular top cap 83 and is held in place by a screw 97 driven therethrough and into threaded engagement with a complementary bore 99 formed in first end 77 of lead screw 27. In use, upper bearing 89 helps maintain lead screw 27 in its proper position and orientation within column 25 while, at the same time, allowing for its axial rotation.

An upper sensor 101 is press fit into an upper sensor sleeve, or housing, 103 which is, in turn, retained in bottom surface 87 of top cap 83 by a screw 105. Preferably, upper sensor 101 is in the form of a magnet switch that is selectively triggered by a complementary magnetic element on carriage 33. Once triggered, upper sensor 101 transmits a signal to control system 36 to terminate activation of drive mechanism 31 and thereby limit further upward displacement of carriage 33, as will be described further in detail below.

Referring now to FIGS. 2(b), 2(c), 6 and 7, drive mechanism 31 is mounted onto support block 37 and serves to rotatably drive lead screw 27. Drive mechanism 31 includes a motor 105 that is fixedly mounted onto top surface 41 of support block 37 so as to partially project into recess 45. Motor 105 rotatably drives a belt 107 that, in turn, engages an annular pulley 109 which is fixedly secured onto second end 79 of lead screw 27 (e.g., by screws).

Figure 6:
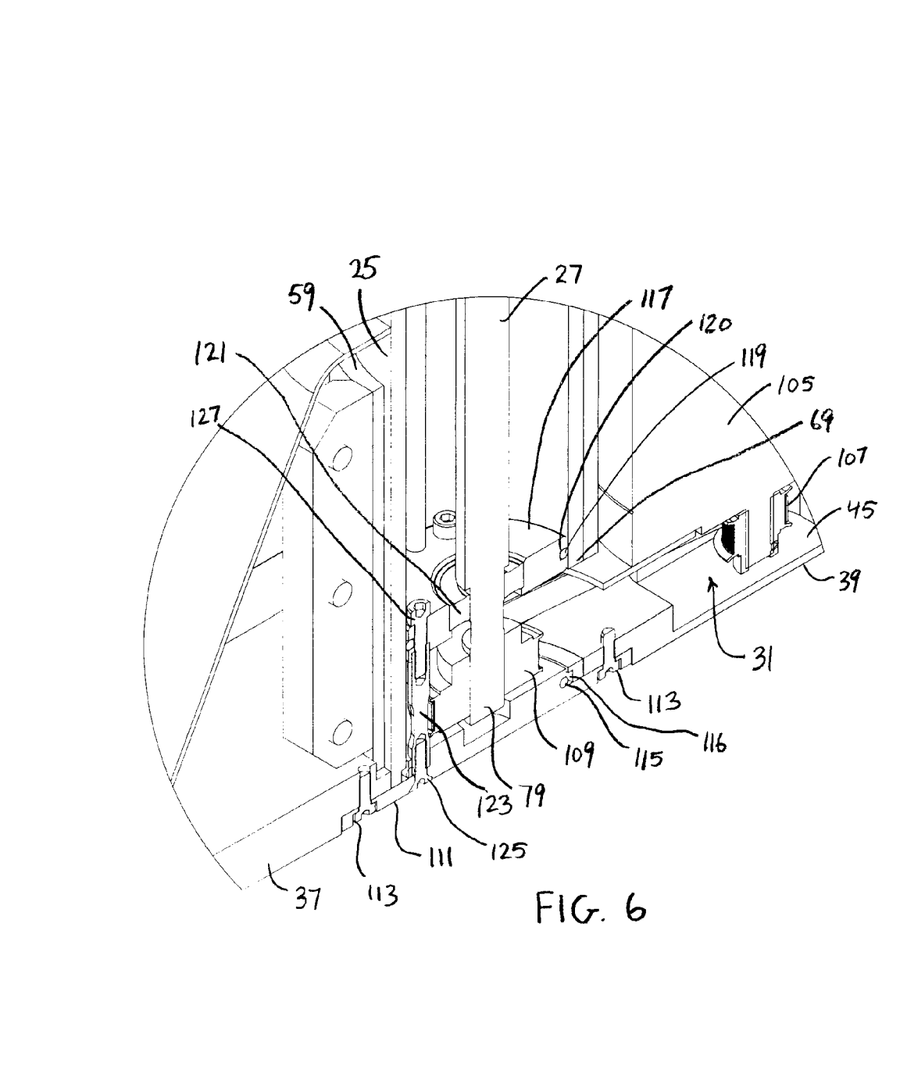
FIG. 6 is an enlarged, fragmentary, section view of the lift shown in FIG. 2(b), taken within the circled region identified by reference letter B.
Figure 7:
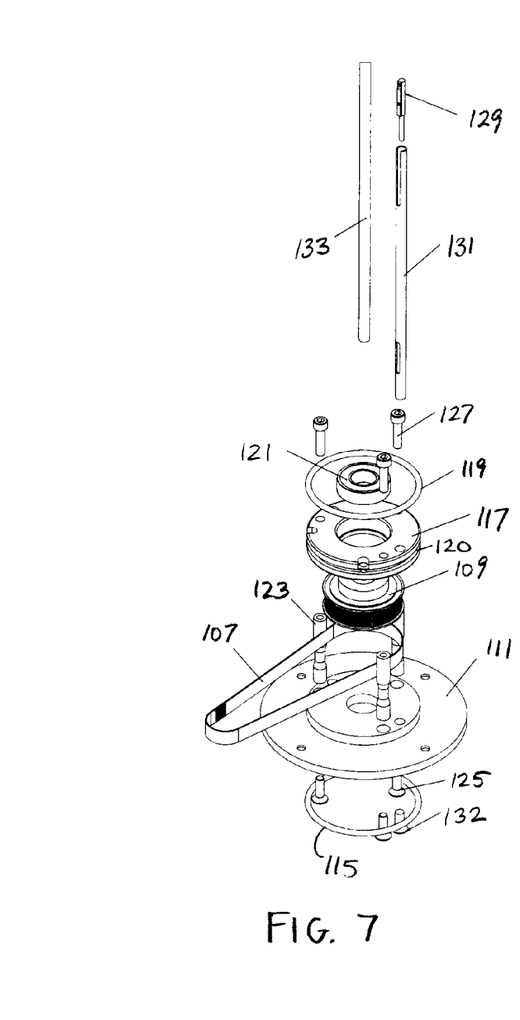
FIG. 7 is an enlarged, exploded, top perspective view of selected components of the drive mechanism shown in FIG. 6.

A disc-shaped, bottom cap 111 is disposed against bottom surface 39 in coaxial alignment with post 59 and is fixedly secured to support block 37 by screws 113. A suitable seal is established between bottom cap 111 and support block 37 by disposing an O-ring 115 within a complementary groove 116 formed in support block 37.

An annular lower bearing mount 117 is press fit into open first end 69 of column 25, with an adequate seal established between lower bearing mount 117 and column 25 by disposing an O-ring 119 within a complementary external groove 120 formed in the periphery of mount 117. An annular lower bearing 121 is retained concentrically within mount 117 by a press fit relationship such that second end 79 of lead screw 27 extends axially through lower bearing 121. Mounted as such onto second end 79, lower bearing 121 helps maintain lead screw 27 in its proper position and orientation within column 25 while, at the same time, allowing for its axial rotation.

A plurality of spindle-shaped standoffs 123 extend orthogonally between bottom cap 111 and lower bearing mount 117 and serve to maintain adequate spacing being pulley 109 and lower bearing 121. Each standoff 123 is secured to bottom cap 111 at one end by a first screw 125 and is secured to lower bearing mount 117 at its opposite end by a second screw 127.

A lower sensor 129 is press fit into a lower sensor sleeve, or housing, 131 which is, in turn, retained within a corresponding bore formed in lower bearing mount 117 by a screw 132. Lower sensor 129 is similar to upper sensor 101 in that lower sensor 129 is preferably in the form of a magnet switch that is selectively triggered by a complementary magnetic element on carriage 33. Once triggered, lower sensor 129 transmits a signal to control system 36 to terminate activation of drive mechanism 31 and thereby limit further downward displacement of carriage 33, as will be described further in detail below.

In addition, an elongated wire duct 133 is press fit into a corresponding bore formed in lower bearing mount 117. Wire duct 133 extends longitudinally through interior cavity 74 along the majority of its length and is dimensioned to receive wiring from upper sensor 101 for retentive and protective purposes.

Figure 8A:
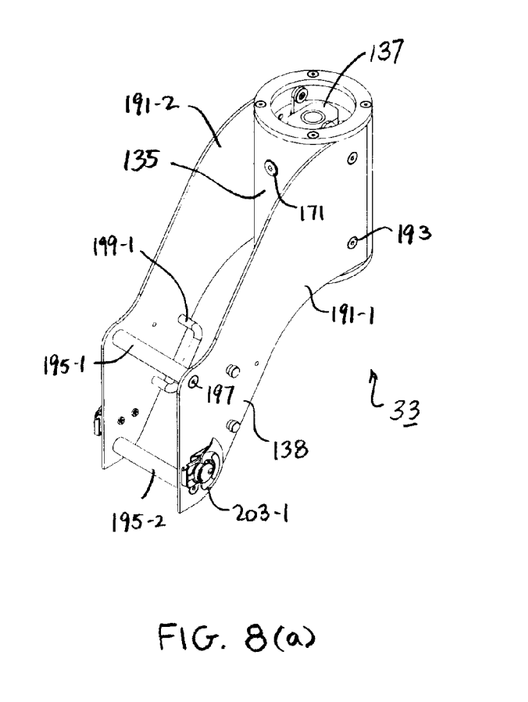
FIGS. 8(a) and 8(b) are assembled, top perspective and exploded top perspective views, respectively, of the carriage shown in FIG. 2(c)
Figure 8B:
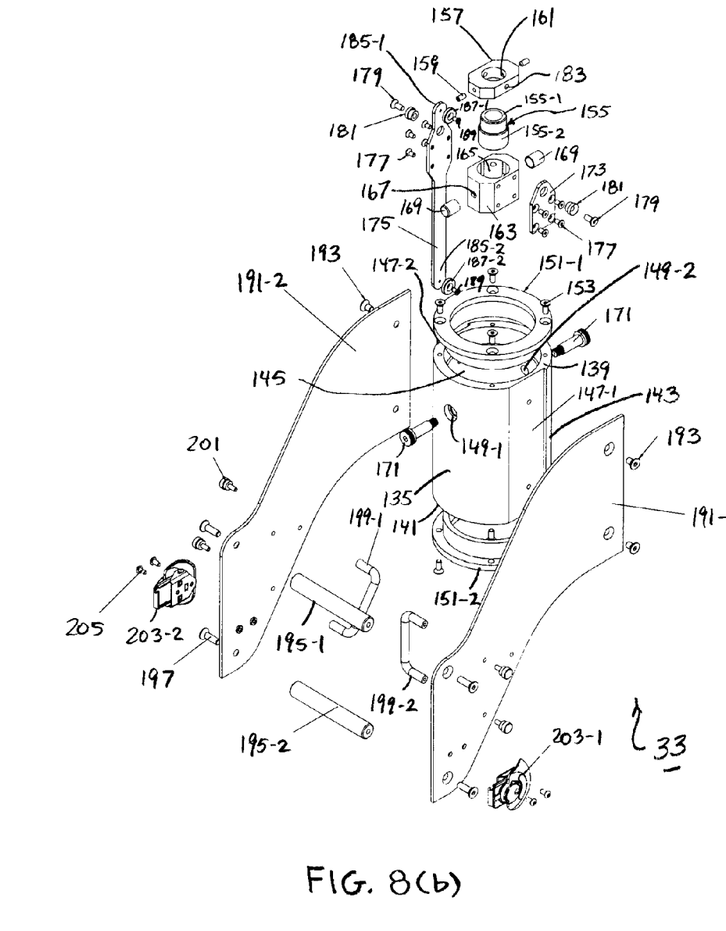

Referring now to FIGS. 2(c), 8(a) and 8(b), carriage 33 is a unitary member that is mounted on column 25 and designed to slide along a portion of its length in a predefined, multi-planar path. Carriage 33 comprises an elongated cylindrical sleeve 135 dimensioned to coaxially slide over column 25 in a telescoping relationship relative thereto, a floating mount 137 disposed within sleeve 135 that engages lead screw 27 and travels along a portion of its length during operation of lift 21-1, and a bracket 138 connected to the exterior of sleeve 135 that is adapted to support platform 35.

Sleeve 135 is constructed as a rigid and durable cylindrical member that includes an open top end 139, an open bottom end 141 and a generally rounded intermediate portion 143 that together define a central, longitudinal interior channel 145. Intermediate portion 143 is preferably shaped to define a pair of opposing flattened regions 147-1 and 147-2, spaced approximately 180 degrees apart, that serve as mounting surfaces to which bracket 137 is secured. Intermediate portion 143 is additionally shaped to define a pair of transverse through holes, or bores, 149-1 and 149-2, spaced approximately 180 degrees apart, that are provided to facilitate connection of floating mount 137 to sleeve 135.

Interior channel 145 of sleeve 135 is dimensioned to receive tubular column 25 in a telescoping relationship. Preferably, upper and lower annular bearings 151-1 and 151-2 are secured to open top and bottom ends 139 and 141, respectively, by screws 153 and project, at least partially, into interior channel 145. Bearings 151 are dimensioned to contact the exterior of column 25 and are preferably constructed out of a low friction material, such as an acetal resin, to enable sleeve 135 to slide easily along column 25.

As seen most clearly in FIG. 8(b), floating mount 137 is represented herein as a gimbal-style nut that includes a cylindrical mounting nut 155 having an interior diameter of approximately 0.75 inches. Mounting nut 155 is internally threaded along its length and is properly dimensioned to be axially mounted onto lead screw 27 in threaded engagement therewith. Mounting nut 155 includes a top section 155-1 that is externally threaded and a widened bottom section 155-2 that is externally smooth.

An octagonal nut flange 157 is internally threaded and is dimensioned to be axially mounted onto threaded top section 155-1 of floating mount 137 in threaded engagement therewith. One or more hex screws 159 are preferably driven through threaded transverse bores 161 in nut flange 157 and into engagement with mounting nut 155 to retain nut flange 157 fixed in place on section 155-1.

An octagonal nut adaptor 163 includes a longitudinal channel 165 that is dimensioned to loosely receive bottom section 155-2 of mounting nut 155 in a coaxial relationship relative thereto. Nut adaptor 163 is also shaped to define a pair of opposing threaded bores 167. For reasons to become apparent below, a hollow cylindrical guide roller 169 is disposed in coaxial alignment with each threaded bore 167 in nut adaptor 163. In turn, an elongated hex screw 171 is inserted through each bore 149 in sleeve 135, through a corresponding slot 75 in tubular column 25, through a corresponding guide roller 169 and into threaded engagement with its associated bore 167 in nut adaptor 163. In this manner, screws 171 suspend, or float, adaptor 163 within interior channel 145 of sleeve 135 in a coaxial relationship relative thereto.

Opposing mount plates 173 and 175 are provided to pivotally couple nut adaptor 163 to nut flange 157. Specifically, mount plates 173 and 175 are fixedly secured to opposing outer surfaces of nut adaptor 163 by screws 177. Furthermore, a screw 179 is driven through a pivot spacer 181 retained within a corresponding bore in each of mount plates 173 and 175 and, in turn, into threaded engagement within a corresponding hole 183 formed in nut flange 157. In this capacity, nut adaptor 163 is able to rock, or swivel, slightly front-and-back relative to nut flange 157.

In the present embodiment, mount plate 175 is constructed an elongated arm that includes a top end 185-1 and a bottom end 185-2. Top and bottom magnets 187-1 and 187-2 are in turn secured to top end 185-1 and bottom end 185-2, respectively, by screws 189. As will be described further below, magnets 187-1 and 187-2 are designed to trigger upper and lower magnetic switch-type sensors 101 and 129, respectively, when disposed in close proximity thereto.

Mounted in the manner set forth in detail above, floating mount 137 is designed to engage lead screw 27 and thereby enable sleeve 135 to slide on tubular column 25 along the path defined by slots 75. Specifically, referring now to FIGS. 9(*a*), 9(*b*), 10(*a*) and 10(*b*), carriage 33 is shown mounted on column 25 and in mechanical engagement with lead screw 27, with selected components of lift 21-1 broken away in part to facilitate examination of the interrelationship of components.

As can be seen, sleeve 135 is slidably mounted onto column 25, with contact against column 25 preferably limited to upper and lower bearings 151-1 and 151-2 to minimize frictional forces. Furthermore, floating mount 137 is threadingly mounted onto lead screw 27 and is fixedly secured to sleeve 135 by screws 171.

Accordingly, as lead screw 27 rotates about its longitudinal axis, mounting nut 155 (which is retained inside flange 157 and adaptor 163) is vertically driven along a linear path parallel to longitudinal axis $L_A$, with the direction of the vertical path (i.e., upwards or downward) being dependent upon the direction of the lead screw 27 rotation (i.e., clockwise or counterclockwise). As mounting nut 155 travels vertically along lead screw 27, flange 157, adaptor 163 and sleeve 135 are all similarly vertically driven as a result of the interconnection of components within floating mount 137.

Figure 9A:
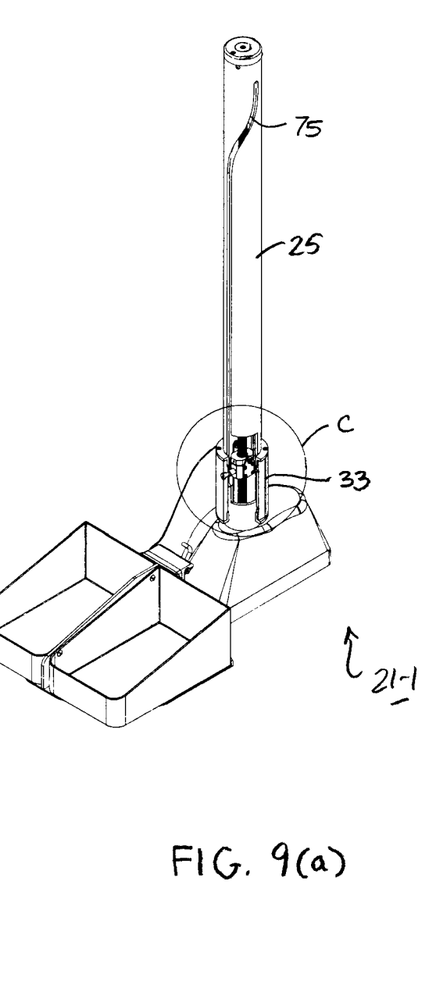
FIG. 9(a) is a front, perspective view of the lift shown in FIG. 2(a), the lift being shown with a portion of the column and the carriage broken away in part in order to help illustrate the interrelation of selected components.
Figure 9B:
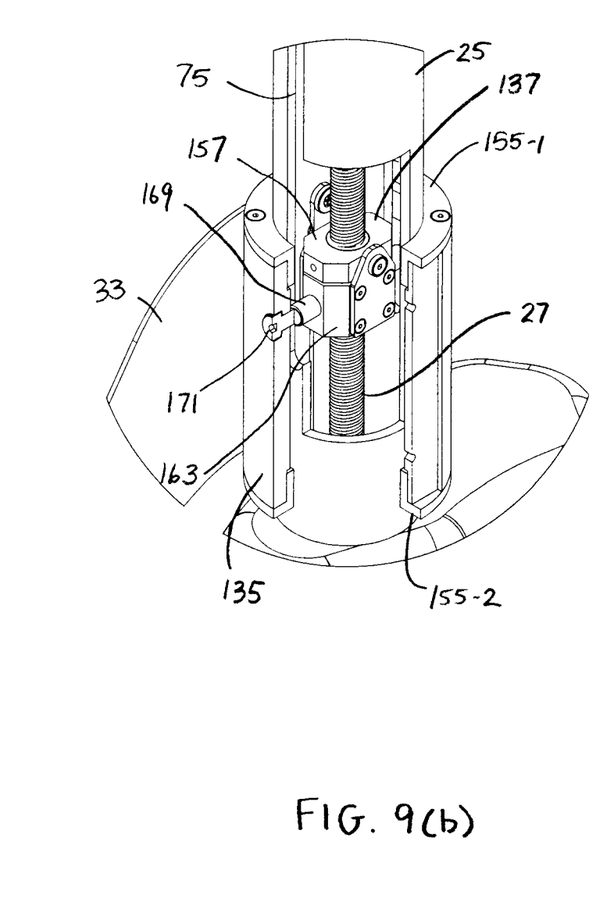
FIG. 9(b) is an enlarged, front perspective view of the lift shown in FIG. 9(a), taken within the circled region identified by reference letter C.
Figure 10A:
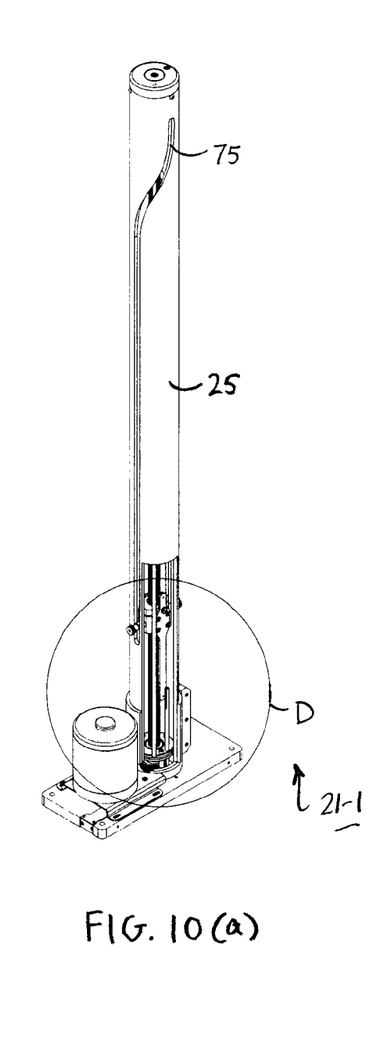
FIG. 10(a) is a rear, perspective view of the lift shown in FIG. 2(a), the lift being shown with a with a portion of the base, column, carriage and platform broken away in part in order to help illustrate the interrelation of selected components.
Figure 10B:
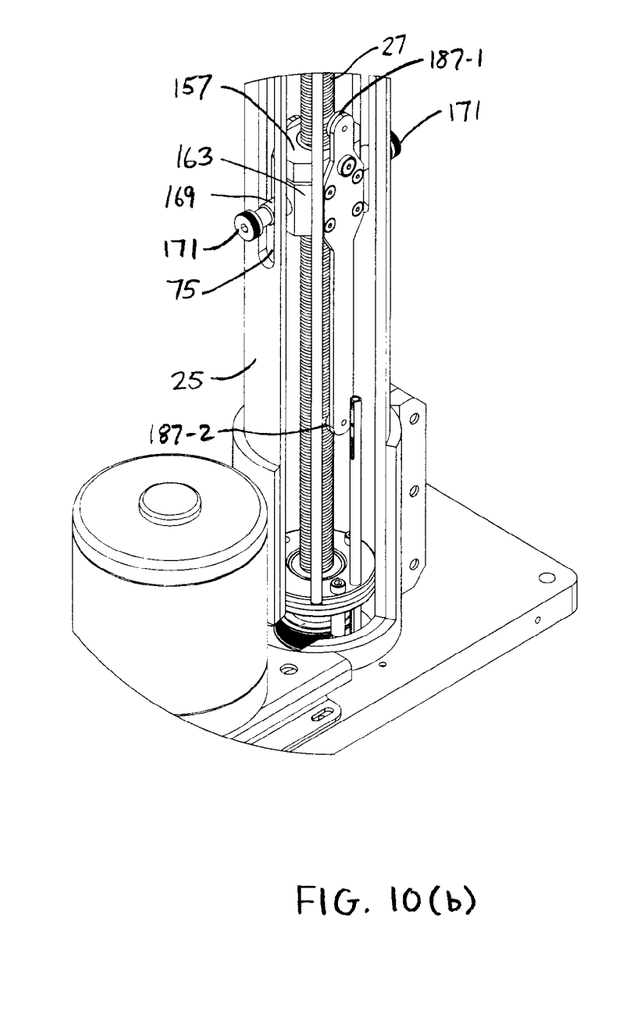
FIG. 10(b) is an enlarged, rear perspective view of the lift shown in FIG. 10(a), taken within the circled region identified by reference letter D.

However, as seen most clearly in FIGS. 9(*b*) and 10(*b*), each guide roller 169 directly aligns within a corresponding slot 75 in column 25. Consequently, as sleeve 135 travels vertically along column 25, the angular position of sleeve 135 relative to longitudinal axis $L_A$ of column 23 adjusts (i.e., rotates) in direct correspondence to the path defined by slots 75. Furthermore, because nut adaptor 163 can swivel slightly in relation to flange 157, guide rollers 169 are able to travel within slots 75 in a smooth and controlled fashion.

Referring back to FIGS. 8(*a*) and 8(*b*), bracket 138 comprises a pair of flattened, plate-like arms 191-1 and 191-2 that are secured to flattened regions 147-1 and 147-2, respectively, of sleeve 135 by screws 193. A pair of spaced apart mount bars 195-1 and 195-2 extends transversely between the distal ends of arms 191 and is secured thereto by screws 197. In addition, a pair of U-shaped handles 199-1 and 199-2 is secured to the inner surface of arms 191-1 and 191-2, respectively, by thumb-type screws 201. Lastly, a pair of latches 203-1 and 203-2 is secured to the outer surface of arms 191-1 an 191-2, respectively, by screws 205 and is provided to releasably secure platform 35 on bars 195, as will be described further below.

Figure 11:
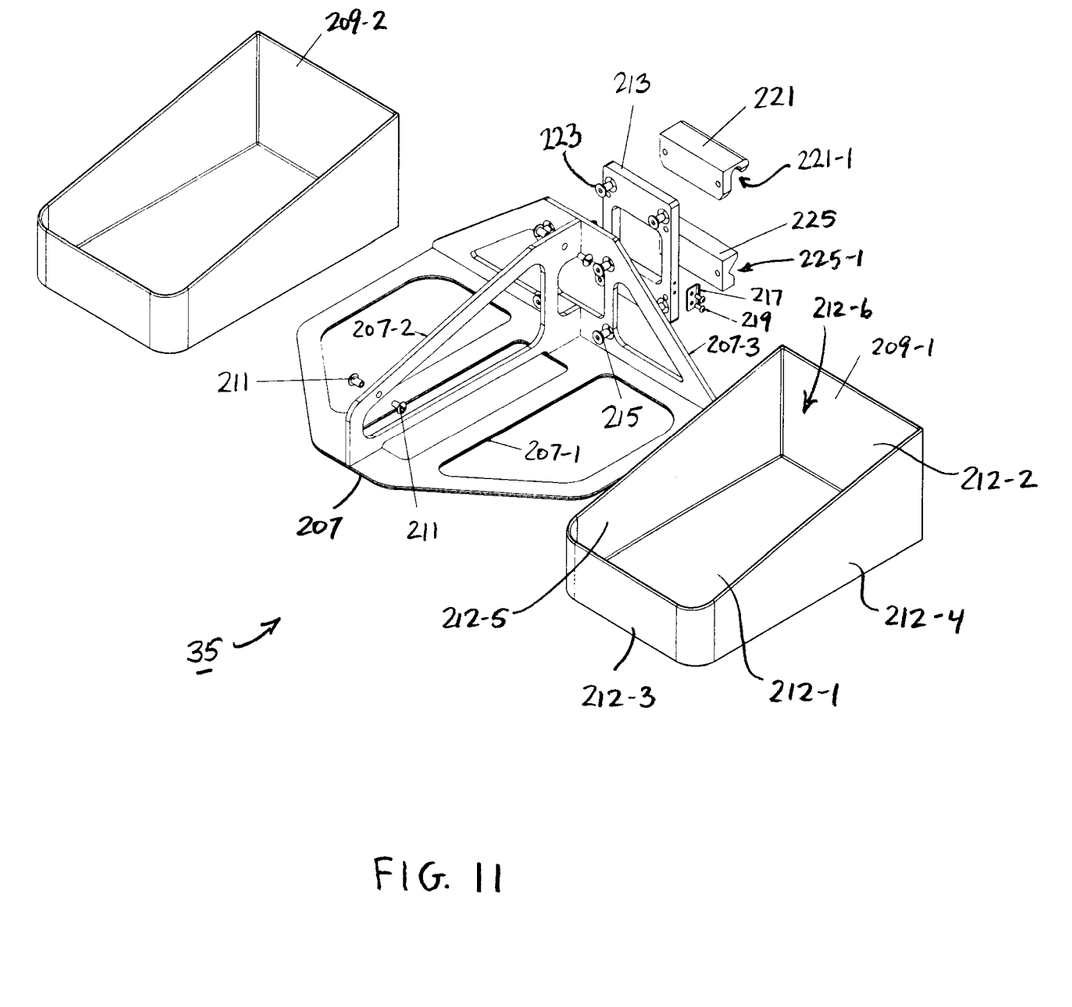
FIG. 11 is an exploded, top perspective view of the platform shown in FIG. 2(c)

Referring now to FIGS. 2(*c*) and 11, platform 35 comprises a frame 207 constructed out of a rigid and durable material, such as plastic. Frame 207 is a unitary member that includes flattened, bottom, or base, wall 207-1 that is horizontally disposed, an upstanding, flattened, center partition wall 207-2 that extends orthogonally away from the approximate centerline of base wall 207-1, and an upstanding, flattened rear wall 207-3 that extends orthogonally away from the rear edge of base wall 207-1.

A pair of trays 209-1 and 209-2 is mounted onto base wall 207-1 on opposite sides of center partition wall 207-2, each tray 109 being fixedly secured to center partition wall 207-2 by screws 211. As can be appreciated, each tray 209 is adapted to retain one or more containers 19 of fluid 17 and is preferably constructed out of a rigid, durable and transparent plastic material to facilitate inspection of fluid levels. In the present embodiment, each tray 209 is shown comprising a flat bottom wall 212-1, a heightened rear wall 212-2, a shortened front wall 212-3, and a pair of opposing, tapered sidewalls 212-4 and 212-5 that together define a shallow cavity 212-6 dimensioned to receive a plurality of containers 19. However, it is to be understood that the dimensions of each tray 209 could be modified to retain various shapes, sizes and numbers of containers 19 without departing from the spirit of the present invention.

An open, square-shaped plate 213 is secured to the rear surface of frame rear wall 207-3 by screws 215. A pair of hook members 217 is mounted onto opposing side edges of plate 213 by screws 219. As will be described further below, each hook member 217 is designed to be releasably engaged by a corresponding latch 203 on bracket 138.

Figure 12A:
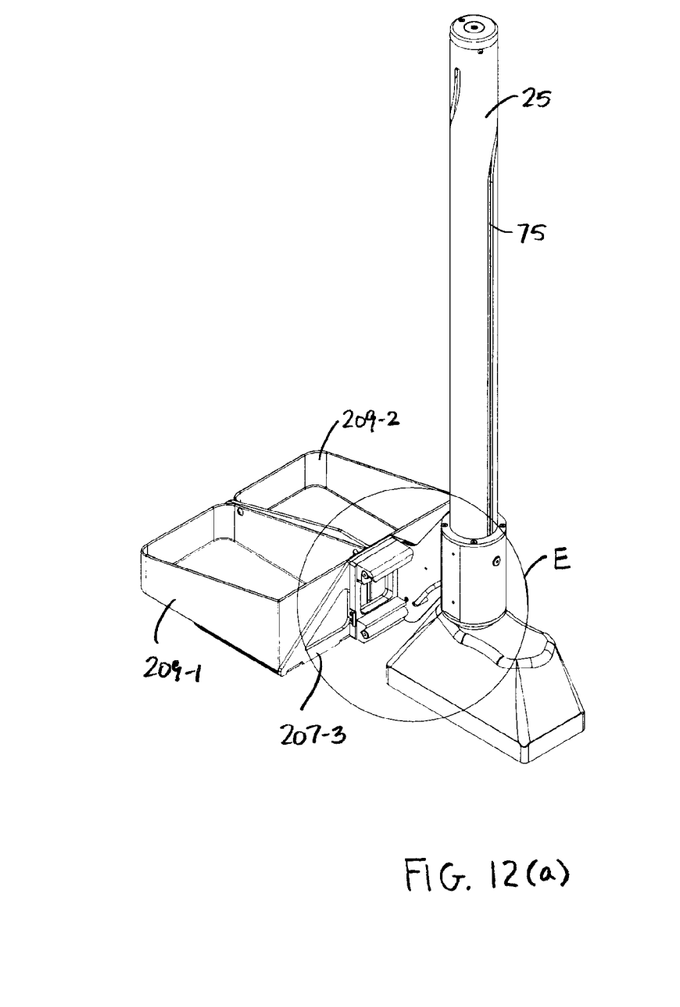
FIG. 12(a) is a rear perspective view of the lift shown in FIG. 2(a), the lift being shown with a portion of the carriage broken away in order to help illustrate the interrelation of selected components.
Figure 12B:
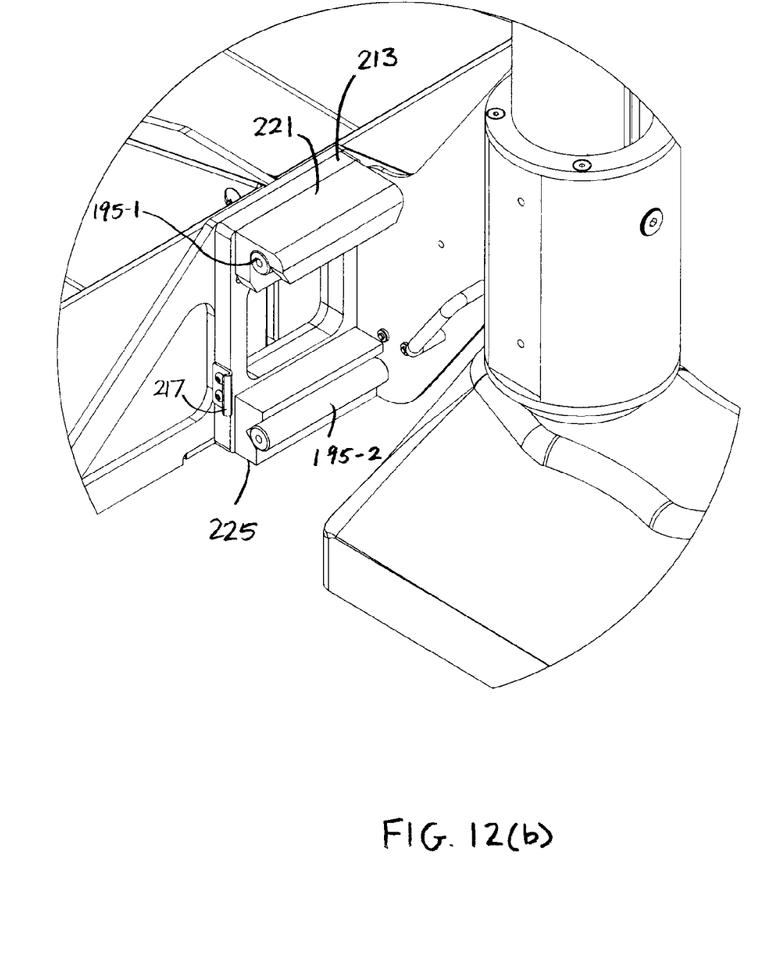
FIG. 12(b) is an enlarged, rear perspective view of the lift shown in FIG. 12(a), taken within the circled region identified by reference letter E.

As seen most clearly in FIGS. 11, 12(*a*) and 12(*b*), an upper mount block 221 is secured to the rear surface of plate 213 by screws 223 and is shaped to define a longitudinal, inverted J-shaped groove 221-1 in its rear surface that is dimensioned to fittingly receive upper mount bar 195-1 on bracket 138. Similarly, a lower mount block 225 is secured to the rear surface of plate 213 by screws (not shown) and is shaped to define a longitudinal, V-shaped groove 225-1 in its rear surface that is dimensioned to fittingly receive lower mount bar 195-2 on bracket 138. Accordingly, it is to be understood that with upper mount bar 195-1 positioned within groove 221-1 and lower mount bar 195-2 positioned within groove 225-1, latches 203 can be disposed in engagement with hook members 217 to secure platform 35 onto carriage 33. However, by disengaging latches 203 from hook members 217, platform 35 can be removed from carriage 33 for repair, replacement or removal of spilled fluid 17 collected therein.

As referenced briefly above, a control system 36 is provided to regulate operation of motorized drive mechanism 31. Referring back to FIG. 1, control system 36 comprises a manually activated, dual-button, membrane-style control switch 229 for initiating movement of platform 35, and any containers 19 retained thereon, either in the upward direction to its elevated position or in the downward direction to its lowered position.

Control system 36 additionally includes a control box 231 that is responsible for regulating operation of motor 105. Control box 231 preferably includes an electronic circuit (not shown) that is internally housed within a protective casing, the electronic circuit comprising, inter alia, a power supply, a motor driver, and a relay circuit. In turn, the electronic circuit is electrically connected by wiring to motor 105, control switch 231, upper sensor 101 and lower sensor 103. Accordingly, it is to be understood that control box 231 regulates the activation and rotational direction of motor 105 in response to signals received from control switch 229, upper sensor 101 and lower sensor 103.

Operation of Lift 21-1

Figure 13A:
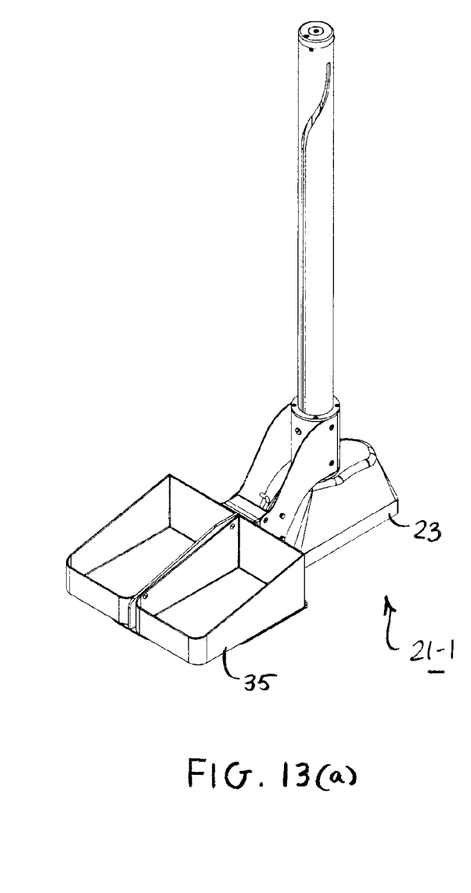
FIGS. 13(a)-(c) are front perspective views of the lift shown in FIG. 12(a) at various stages of its operation.

Lift 21-1 is designed primarily for use in a laboratory environment of the type shown in FIG. 1. Specifically, base 23 is preferably secured to bench top 13-1 in a direct, side-by-side relationship relative to the particular device 15 with which it is to be used. With platform 35 disposed in its lowered position, as shown in FIG. 13(*a*), containers 19 are rendered easily accessible by laboratory technicians to be inspected and, if necessary, replaced or refilled. In addition, any connection of tubing can be secured between containers 19 and device 15.

Figure 13B:
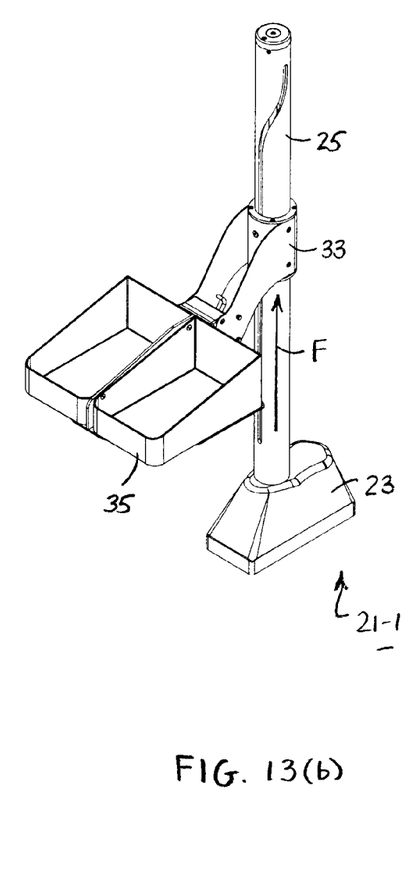
Figure 13C:
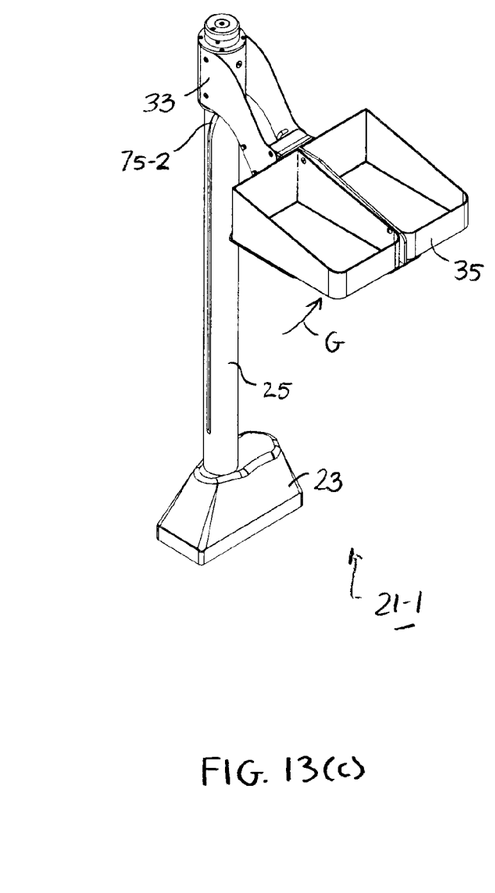

Through activation of control switch 231, drive mechanism 31 rotates lead screw 27 in a first direction which, in turn, initially pulls carriage 33, platform 35 and containers 19 along a linear, vertical path on column 25, as represented by arrow F in FIG. 13(b). As lead screw 27 continues its rotation in the first direction, carriage 33 is then pulled upward and begins to rotate along the 90 degree helical path defined by upper portion 75-2 of slots 75, as represented by arrow G in FIG. 13(c). Once top magnet 187-1 on mount plate 175 is disposed in close proximity to upper sensor 101, an appropriate signal is sent from sensor 101 to a relay circuit in control system 36 which, in turn, results in the deactivation of motor 105 (i.e., to prevent "over-driving"). With motor 105 deactivated, platform 35 is retained in its elevated position with containers 19 disposed in direct alignment above device 15, as shown in FIG. 1.

When lowering of platform 35 is required, the proper button on control switch 231 is activated which, in turn, causes drive mechanism to rotate lead screw 27 in the opposite direction. As lead screw 27 rotates in the opposite direction, carriage 33 is drawn downward along the same path as defined by slots 75. Finally, once lower magnet 187-2 on mount plate 75 is disposed in close proximity to lower sensor 129, an appropriate signal is sent from sensor 129 to control system 36 which, in turn, results in the deactivation of motor 105. With motor deactivated, platform 35 is retained in is lowered position until further movement is required.

Features and Advantages of Lift 21-1

It should be noted that the particular construction of lift 21-1 as well as its operation within system 11 provides a number of notable advantages.

As a first advantage, the ability to mechanical displace containers 19 between a lowered position, which is highly suitable for access by a laboratory technician, and an elevated position, which is highly suitable for the delivery of fluid 17 to device 15 via gravity, significantly enhances laboratory safety, which is highly desirable.

As a second advantage, the bench top footprint required by lift 21-1 is minimal, thereby maximizing the usable area on workspace 13-1 available for laboratory purposes, which is highly desirable. The relatively small bench top footprint for lift 21-1 is achieved, at least in part, by the defined travel path for carriage 33 during operation (and, in particular, the helical component of the travel path).

As a third advantage, the particular design of platform 35 allows for (i) greater ease in monitoring fluid levels due to the transparent construction of trays 209, (ii) greater protection of device 15 due to solid, leak-proof construction of trays 209, and (iii) greater container 19 holding flexibility due to the ability to removably mount different size, shapes and styles of platforms 35 onto carriage 33.

The embodiment shown in the present invention is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A fluid delivery system, comprising:
   (a) a container filled with a fluid;
   (b) a laboratory instrument adapted to receive the fluid;
   (c) a lift for supporting the container, wherein the lift is adapted to transport the container between a lowered position suitable for handling the container and an elevated position suitable for the delivery of the fluid through a fluid line to the laboratory instrument by gravity;
   (d) wherein the lift transports the container between the lowered and elevated positions along a path that includes a linear vertical component and a helical component; and
   (e) wherein the lift comprises:
       (1) a column having a first end, a second end and a longitudinal axis;
       (2) an elongated lead screw that extends longitudinally through the column, the lead screw being adapted for axial rotation;
       (3) a carriage slidably coupled to the column and mechanically coupled to the elongated lead screw; and
       (4) a platform coupled to the carriage for supporting the container;
       (5) wherein rotation of the lead screw slidably displaces the carriage along the column.

2. The fluid delivery system as claimed in claim 1, wherein the lift transports the container between the lowered and elevated positions along a predefined, multi-planar path.

3. The fluid delivery system as claimed in claim 1, wherein the laboratory instrument and the lift are mounted onto a common support structure in a side-by-side relationship.

4. The fluid delivery system as claimed in claim 1, wherein rotation of the lead screw displaces the carriage along a path that, at least in part, rotates about the longitudinal axis defined by the column.

5. The fluid delivery system as claimed in claim 4, wherein the lift further comprises a base for retaining the first end of the column.

6. The fluid delivery system as claimed in claim 5, wherein the base defines the footprint for the lift, the base having a length of approximately 350 mm and a width of approximately 155 mm.

7. The fluid delivery system as claimed in claim 4, wherein the column is in the form of a hollow tubular member that is shaped to include a continuous slot along a portion of its length.

8. The fluid delivery system as claimed in claim 7, wherein the slot includes a straightened portion and a helical portion.

9. The fluid delivery system as claimed in claim 7, wherein the carriage comprises:
   (a) an elongated cylindrical sleeve slidably mounted over the column; and
   (b) a floating mount coupled to the sleeve, the floating mount being axially mounted onto the lead screw in threaded engagement therewith;
   (c) wherein rotation of the elongated lead screw vertically displaces the floating mount along at least a portion of the length of the lead screw.

10. The fluid delivery system as claimed in claim 9, wherein the floating mount includes a guide roller that fittingly projects through the slot in the column.

11. The fluid delivery system as claimed in claim 10, wherein, as the floating mount travels vertically along at least a portion of the lead screw, the guide roller rotates the sleeve about the longitudinal axis defined by the column in order to remain within the slot.

12. The fluid delivery system as claimed in claim 4, wherein a cap assembly is fixedly mounted onto the second end of the column, the cap assembly supporting the lead screw in place within the column.

13. The fluid delivery system as claimed in claim 4, further comprising a drive mechanism for selectively rotating the lead screw.

14. The fluid delivery system as claimed in claim 13, wherein the drive mechanism comprises a motor that is coupled to the drive screw.

15. The fluid delivery system as claimed in claim 14, further comprising a control system for regulating operation of the drive mechanism.

16. The fluid delivery system as claimed in claim 4, wherein the platform is removably coupled to the carriage.

17. A lift for a fluid delivery system, the fluid delivery system comprising a container filled with a fluid and a laboratory instrument adapted to receive the fluid, the lift comprising:
(a) a column having a first end, a second end and a longitudinal axis;
(b) an elongated lead screw that extends longitudinally through the column, the lead screw being adapted for axial rotation;
(c) a carriage slidably coupled to the column and mechanically coupled to the elongated lead screw; and
(d) a platform coupled to the carriage, the platform being adapted to support the container;
(e) wherein rotation of the lead screw slidably displaces the carriage along the column and transports the container between a lowered position suitable for handling the container and an elevated position suitable for the delivery of the fluid through a fluid line to the laboratory instrument by gravity; and
(f) wherein the lift transports the container between the lowered and elevated positions along a path that includes a linear vertical component and a helical component.

18. The lift as claimed in claim 17, wherein rotation of the lead screw displaces the carriage along a path that, at least in part, rotates about the longitudinal axis defined by the column.

* * * * *